United States Patent
Park et al.

[19]

[11] Patent Number: 5,142,899
[45] Date of Patent: Sep. 1, 1992

[54] AUTOMATIC VISCOSITY MEASURING DEVICE

[75] Inventors: Su C. Park; Young M. Kuon; Jin H. Kim, all of Korea, Rep. of Korea

[73] Assignee: SKC Limited, Rep. of Korea

[21] Appl. No.: 619,177

[22] Filed: Nov. 27, 1990

[30] Foreign Application Priority Data

Nov. 27, 1989 [KR] Rep. of Korea ............ 89-17243

[51] Int. Cl.[5] .................................. G01N 11/04
[52] U.S. Cl. ........................................... 73/55
[58] Field of Search ............... 73/54, 55, 56; 364/556

[56] References Cited

U.S. PATENT DOCUMENTS

| | | |
|---|---|---|
| 3,604,247 | 9/1971 | Gramain ................. 73/55 |
| 3,713,328 | 1/1973 | Aritomi .................. 73/55 |
| 3,798,960 | 3/1974 | Glass ..................... 73/55 |
| 3,908,441 | 9/1975 | Virloget .................. 73/55 |
| 4,425,790 | 1/1984 | Bice et al. ............... 73/55 |

OTHER PUBLICATIONS

Grinnell Jones and S. K. Talley "The Automatic Timing of the Ostwald Viscometer by Means of Photoelectric Cell" Journal of Physics vol. 4 (Jun. 1933) pp. 215-224.

Primary Examiner—Michael Razavi
Assistant Examiner—Raymond Y. Mah
Attorney, Agent, or Firm—Quarles & Brady

[57] ABSTRACT

An automatic viscosity measuring device which measures sample levels, automatically fills a sample to a marked line by vacuum pressure, automatically counts the time for the sample to fall by a sensor in the upper and lower marked lines, finds intrinsic viscosity by concentration and then measures the degree of error from relative viscosity in the case of the Ostwald's viscosimeter, which automatically measures the viscosity of a high molecular material.

3 Claims, 5 Drawing Sheets

AUTOMATIC VISCOSITY MEASURING DEVICE

BACKGROUND OF THE INVENTION

1. Field of the Invention

The present invention relates to an automatic viscosity measuring device which automatically controls the filling of a sample up to an upper marked line and determines the intrinsic viscosity thereto by correctly measuring the time elapsed as the sample falls to a final marked line and then makes the degree of error known by comparing a difference from relative viscosity in the case of the Ostwald's viscosimeter, which automatically measures the viscosity of a high molecular material.

2. Brief Description of the Prior Art

For measurement of viscosity heretofore, the Ostwald's viscosimeter has been used generally. It measures the time for a given volume of high molecular material to flow through a vertical capillary under gravity. The relative viscosity of a liquid substance at a particular temperature is found by measuring the time it takes the liquid to flow down in a viscosimeter at said particular temperature and the time for water of the same volume to flow down in the same viscosimeter at 25° C. Absolute viscosity is found by multiplying it by the viscosity of water for the relative viscosity of the sample substance.

A device which measures the viscosity of a liquid in a container by means of a temperature sensor and a detecting circuit associated therewith is also known widely.

However, these prior viscosity measuring devices are unable to control the automatic filling of liquid to an upper marked line of an Ostwald's viscosimeter and to correctly measure the time for the filled liquid to fall to a lower marked line.

BRIEF DESCRIPTION OF THE PRESENT INVENTION

The present invention provides a device which measures sample levels, in a viscosimeter automatically fills a sample to an upper marked line by vacuum pressure, automatically counts the time for the sample to fall to a lower marked line by a sensor connected to the upper and lower marked lines, finds intrinsic viscosity by concentration and then measures the degree of error from relative viscosity in the case of the Ostwald's viscosimeter.

DETAILED DESCRIPTION OF THE PREFERRED EMBODIMENTS

The present invention will now be described in detail according to the drawings attached hereto.

In FIG. 1, 1 to 4 viscosimeters can be installed in a water bath(30) for the convenience of a user to measure the viscosity of different samples. In case of necessity, up to 32 viscosimeters can be installed.

The present invention enables the Ostwald's viscosimeter (20) to be kept at a desired temperature by the water bath(30) which is controlled at a high precision of ±0.01° C.

The water contained in the water bath(30) must be distilled to promote the purity of temperature. The level of this water must reach above the upper marked line(D) of Ostwald's viscosimeter(20).

In order to measure a sample, the sample contained in the Ostwald's viscosimeter(20) must be left at a water temperature of 30° C. for about 30 minutes so as to achieve thermal balance with the water bath (30).

Sample measurement control in the present invention controls a pump(42), a solenoid valve(41) and an optical sensor(43), which are within a control unit(40), by the simple operation of a computer(10).

The computer(10) applied in the present invention is 16 bits for data processing and system control.

The computer(10) automatically stores a compensating coefficient proper to the Ostwald's viscosimeter(20), namely, a compensating coefficient which varies according to the volume from the upper marked line(D) to the lower marked line(E) of the viscosimeter 20 and a compensating coefficient measured by an actual user and counts the time for a sample to fall from the upper marked line (D) to the lower marked line(E) of the Ostwald's viscosimeter(20)

A timer within the computer(10) is more precise than 1/100 second. It has high reproducibility which amounts to less than 1/10 in error when a sample is measured.

After the sample is measured, falling time is automatically stored and relative viscosity is automatically calculated according to the falling time(T).

Figure 1:
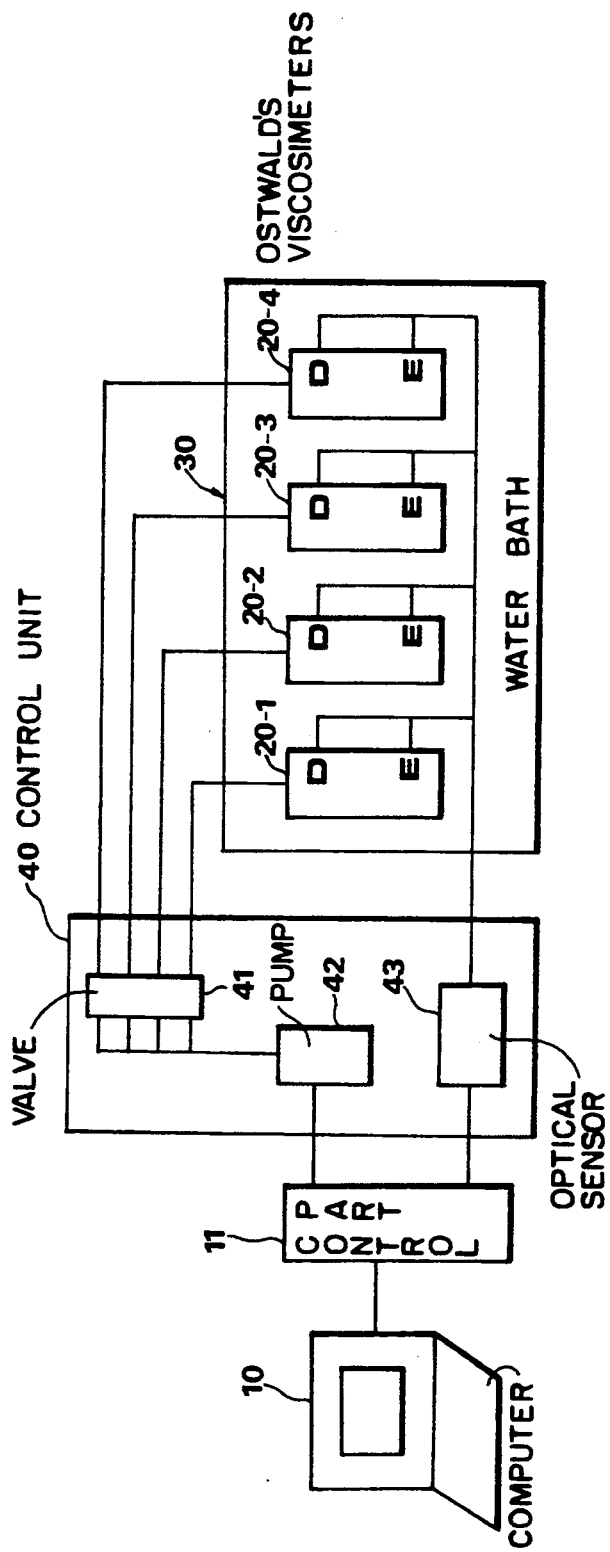
FIG. 1 is a systematical view of the present invention.
Figure 2:
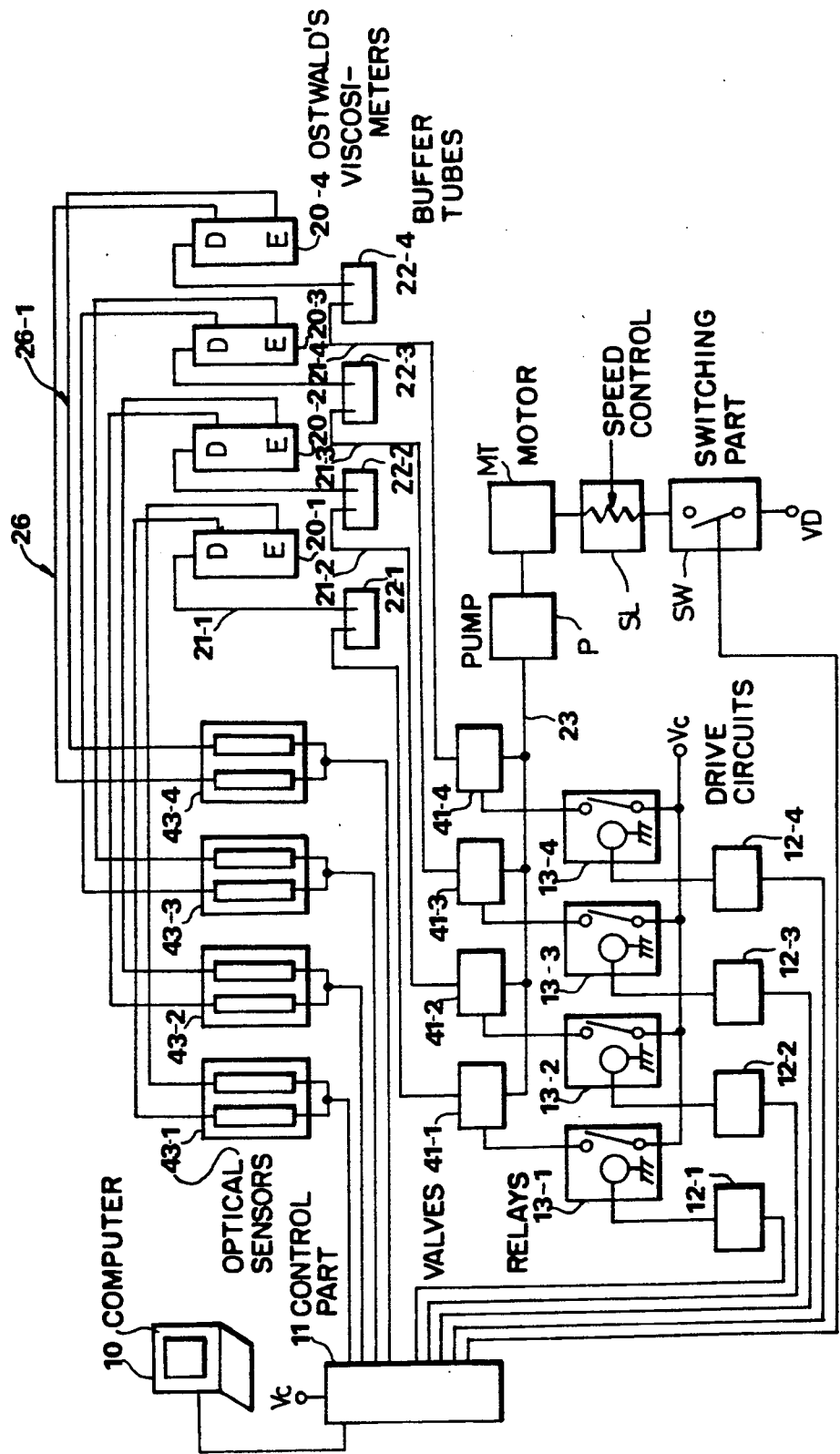
FIG. 2 is a block diagram of the present invention.

FIG. 2 illustrates a more concrete form of the present invention. In this example, four Ostwald's viscosimeters(20-1)-(20-4) are applied.

For the four viscosimeters, the computer(10) generates or puts a signal which drives four optical sensors(43-1)-(43-4) and drives circuits(12-1)-(12-4) through an input/output control part (11).

Figure 3:
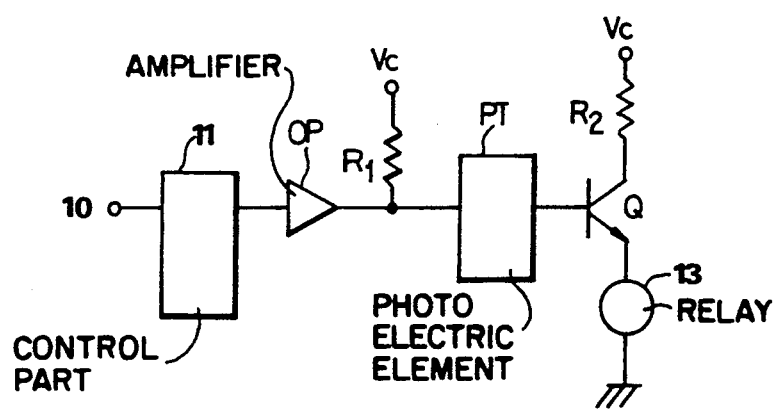
FIG. 3 is a detailed diagram of a drive circuit of the present invention.

The drive circuits(12-1)-(12-4) include an amplification part(OP) which amplifies a signal output from the input/output control part(11) and a photoelectric element(PT) which operates by this signal, as illustrated in FIG. 3.

A transistor(Q) will be connected to the output port of photoelectric element(OP), and relays(13-1)-(13-4) which control the shortcircuiting and opening of solenoid valves(41-1)-(41-4) will be connected to the emitter port of the transistors(Q).

The input/output ports of the solenoid valves(41-1)-(41-4) which are made to open and shortcircuit by the operation of relays (13-1)-(13-4), are connected by air pressure lines(23), (21-1)-(21-4) and each input port is connected in parallel from one vacuum pump(P).

The maximum suction pressure of this vacuum pump(P) is $0g/cm^2$-1 $kg/cm^2$.

In the present invention, the vacuum pump(P) turns a switching part(SW) on.

Accordingly, a motor(MT) connected to a speed controller(SL) starts and causes the vacuum pump(P) to generate such vacuum pressure as stated above.

The speed controller(SL) controls pressure in the air pressure lines(23), (21-1)-(21-4) according to a viscosity coefficient of a sample.

If such vacuum pressure control fails and the sample which is small its coefficient of viscosity is drawn in by great vacuum pressure, the sample will flow backward through the air pressure lines(21-1)–(21-4) and solenoid valves(41-1)–(41-4) and overflow in the direction of the vacuum pump(P).

It is therefore desirable that a separate buffer device be installed between the solenoid valves(41-1)–(41-4) and the Ostwald's viscosimeters(20-1)–(20-4).

Figure 4:
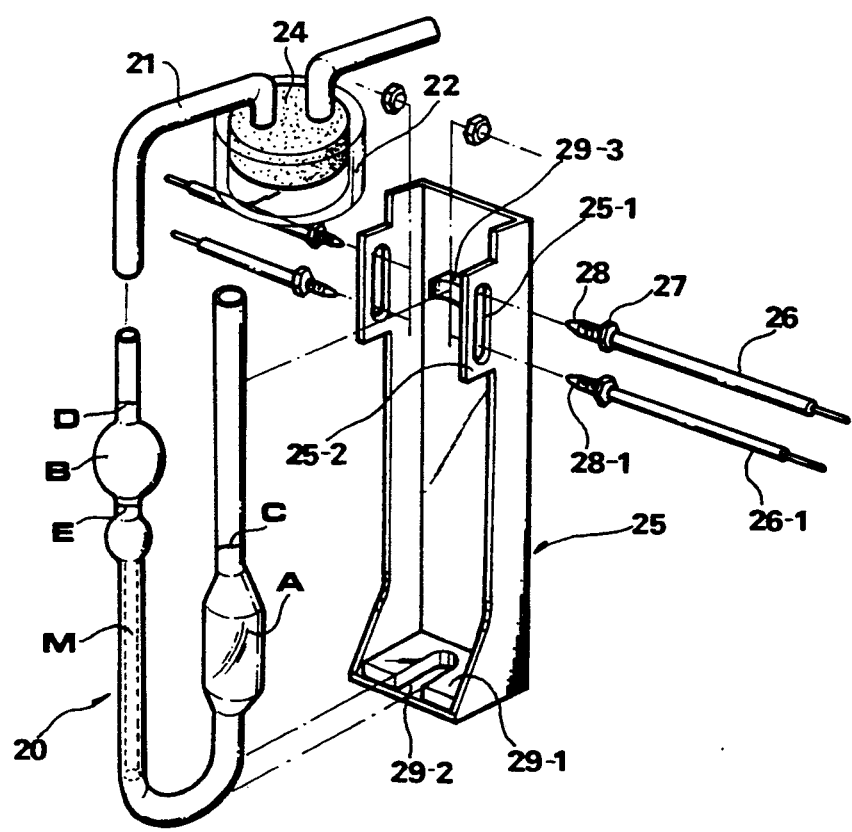
FIG. 4 is a perspective view showing a fixing bracket, a buffer tube and an Ostwald's viscosimeter of the present invention.

In the present invention, a buffer tube(22) which will be connected to the Ostwald's viscosimeter(20) by an air pressure line(21) is installed, as illustrated in FIG. 4. The buffer tube (22) will be formed into a cylindrical tube with one side tightly closed and its volume must be made not to exert a great influence upon the initial resonance pressure of the vacuum pump(P).

The buffer tube(22) will be tightly closed by forcibly inserting into the open part of the buffer tube(22) a rubber stopper into which the air pressure line(21) which is connected from a solenoid valve(41) and one end of the air pressure line(21) which is connected from the side of the Ostwald's viscosimeter(20) are fixed.

Consequently, pressure in the vacuum pump(P) is impressed on the Ostwald's viscosimeter(20) through the buffer tube(22).

When the Ostwald's viscosimeter(20) is installed in the water bath(30), it is securely held by a fixing bracket(25) shaped as shown in FIG. 4. The Ostwald's viscosimeter(20) is initially filled by adding liquid to the open top of the volume tube A of the viscosimeter(20). The upper and lower marked lines(D) and(E) of the Ostwald's viscosimeter(20) are made to fac to the front for observation. The lower part of the U-shaped tube must be fixed in a fixing groove (29-2) formed in the fixing piece(29-1) of the fixing bracket(25).

An adjusting aperture(25-1) is formed in the upper and lower parts of an adjusting piece(25-2) projecting on opposite sides facing to the front in the upper part of the fixing bracket(25). An optical fiber(26) with detects the upper marked line(D) of Ostwald's viscosimeter(20) and an optical fiber(26-1) which detects the lower marked line(E) thereof will be installed so as to oppose in the upper and lower sides of the adjusting piece(25-2). The optical fibers (26) and (26-1) and the adjusting piece(25-2) will be fixed by an optical fiber fixing connector(27). The connector(27) will adjust not only the length of the signal detection ports(28) (28-1) of optical fibers (26) and (26-1).

The signal detection ports(28) and (28-1) of the optical fibers (26) and (26-1) are made to correspond with each other. Infrared signals sent out from optical sensors(43-1)–(43-4) are thereby transmitted through the upper marked line(D) or the lower marked line(E).

At this time, a sample detection signal is made low.

The Ostwald's viscosimeter(20) installed closely to the fixing bracket(25) as mentioned above will remarkably reduce the influence exerted by an outside vibration and keep itself from leaning to the front by being supported by a fixing piece(29-1) and a supporting piece(29-3) in a condition where it is fixed into a fixing groove(29-2).

Figure 5:
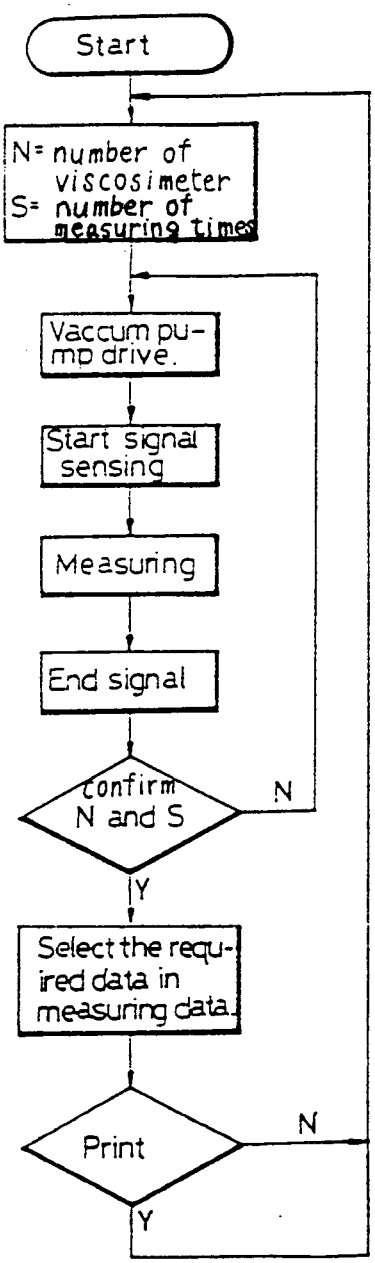
FIG. 5 is a flow chart of the present invention.

Referring to the measuring operation of the present invention, if the computer(10) outputs an initial vacuum pump(P) driving signal, the input/output control part(11) turns the switching part(SW) on and power is supplied to the motor(MT) through the speed controller(SL), as illustrated in FIG. 5.

At this time, the speed controller(SL) is adjusted to a voltage suitable for the viscosity characteristics of a sample.

Accordingly, by the start of the motor(MT), the vacuum pump (P) generates vacuum pressure. The input/output control part (11) operates the optical sensors(43-1)–(43-4) which have a photosensor part for the upper marked line(D) and photosensor part for the lower marked line(E) and sends infrared signals to the signal detection ports(28) and (28-1) through the optical fibers(26) and (26-1) The corresponding signal detection ports(28) and (28-1) detect the position of a sample.

When the switching part(SW) turns on, the computer(10) outputs an operation signal to a solenoid valve (41-1) through the input/output control part(11).

The above signal operates a photoelectric element(PT) after amplification in an amplifier(OP).

Consequently, the transistor(Q) turns on and the relay(13-1) operates. The supply power source(Vc) excites the solenoid valve (41-1) through a contact point of relay(13-1) which turns on and a spool (not illustrated) is thereby opened. Vacuum pressure generated in the air pressure line(23) by the vacuum pump(P) is delivered to the Ostwald's viscosimeter(20-1) through an air pressure line(21-1) and a buffer tube(22-1).

By the above operation, a sample in the A volume tube of Ostwald's viscosimeter(20-1) with its one side open is filled up in the B volume tube through a capillary tube(M).

When the sample in the B volume tube passes the lower marked line(E), the infrared signal which is sent to the signal detection port(28-1) of the optical fiber (26-1) on the other side through the detection port(28-1) is intercepted, so that the photosensor part in the lower marked line (E) of the optical sensor(43-1) inputs a low level signal to the input/output control part(11).

Accordingly, as the low level signal sent, the input/output control part(11) receives a control signal from the computer (10) and demagnetizes the switch(SW), relay(13-1) and solenoid valve(41-1).

Consequently, the pressure in air pressure line(21-1) becomes atmospheric pressure through the demagnetized solenoid valve(41-1), and the sample in the B volume tube flows through the capillary by the force of gravity.

At this time, the sample filled to the upper marked line (D) falls, and the intercepted infrared signal of the signal detection port(28) is transmitted to the optical fiber(26) through the signal detection port(28) on the other side. Then, the photosensor part in the upper marked line(D) of the optical sensor (43-1) generates a high level signal and sends it to the input/output control part(11).

In that case, the input/output control part(11) inputs to the computer(10) a signal which is input from the optical sensor (43-1). The computer(10) recognizes a detection signal in the upper marked line(D) by the aforesaid signal and performs counting operation as a separate timer function and, at the same time, displays a counting process on a monitor as an on-screen display function of memory map.

Furthermore, when the sample contained in the B volume tube flows into the capillary(M) by means of gravity and the upper end of the sample passes through the lower marked line(E), the infrared signal of the signal detection port(28-1) is input to the lower marked line(E) photosensor part of the optical sensor (43-1) through the optical fiber(26-1) and an infrared detection signal is thereby generated.

When a high level detection signal generated in such a manner is input into the computer(10) through the input/output control part(11), the counting operation ends, and the counted time is displayed on the monitor as a memory map function.

By the above operation, the time for a sample to fall to the lower marked line(E) from the upper marked line(D) is measured.

After the aforesaid operations are performed, the computer(10) operates the next solenoid valve(41-2) and motor(MT) as a program illustrated in FIG. 5 and repeats the above mentioned operations.

When the four Ostwald's viscosimeters (20-1)-(20-4) sample falling measurements are performed by the aforesaid operations, the computer(10) outputs a routine signal according to the number of measurements programmed as in Table 1 and repeats the aforesaid operations in consecutive order.

In the following Table 1, falling time according to the number of measurements is shown.

TABLE 1

|   | 1 | | 2 | | 3 | | 4 | |
|---|---|---|---|---|---|---|---|---|
|   | time (sec) | variation | time (sec) | variation | time (sec) | variation | time (sec) | variation |
| 1 | *45.04 | 1.000 | *43.31 | 1.000 | *49.18 | 1.000 | *63.82 | 1.000 |
| 2 | *45.04 | 1.000 | *43.30 | 1.000 | *49.18 | 1.000 | *63.81 | 1.000 |
| 3 | 45.03 | 1.000 | 43.30 | 1.000 | 49.18 | 1.000 | 63.81 | 1.000 |
| 4 | 45.03 | 1.000 | 43.31 | 1.000 | 49.18 | 1.000 | 63.81 | 1.000 |
| 5 | 45.03 | 1.000 | 43.31 | 1.000 | 49.18 | 1.000 | 63.80 | 1.000 |
| 6 | 45.03 | 1.000 | 43.30 | 1.000 | 49.20 | 1.000 | 63.81 | 1.000 |
| 7 | 45.03 | 1.000 | 43.31 | 1.000 | 49.19 | 1.000 | 63.81 | 1.000 |
| 8 | 45.03 | 1.000 | 43.31 | 1.000 | 49.18 | 1.000 | 63.80 | 1.000 |
| 9 | 45.04 | 1.000 | 43.31 | 1.000 | 49.19 | 1.000 | 63.80 | 1.000 |
| 10 | 45.03 | 1.000 | 43.31 | 1.000 | 49.18 | 1.000 | 63.80 | 1.000 |
| average value | 45.04 | 1.000 | 43.31 | 1.000 | 49.18 | 1.000 | 63.81 | 1.000 |

When an error is great in average value (when it is recognized as an erroneous data), it is excepted.

Here, the average indicates the statistics of time shown through a falling test given ten times.

Thus, in the present invention, falling of a sample is automatically measured.

Table 2 shows that the relative viscosity of a sample is calculated when the falling time measured as above is applied to the following formula:

$$\frac{B \times t_1 - \frac{C}{t_1}}{B \times t_0 - \frac{C}{t_0}} = \text{Viscosity coefficient}(\eta_r) \quad \text{formula (1)}$$

$\eta_r$: relative viscosity
B: Coefficient of compensation
$t_0$: falling time measured of O.C.P(sec)
C: 2.4(constant)

When relative viscosity is known by substituting a measured value for the above formula, absolute viscosity can be found by looking at it on a chart(not illustrated).

Although calculation of relative viscosity and absolute viscosity by falling time measured according to the present invention is made possible by setting a program in the computer(10), it is briefly described by a vertical calculation method here.

Another embodiment of the present invention will now be described.

The relative viscosity of a sample will be found by a measuring device according to the present invention.

To do so, samples to be tested are filled in the four Ostwald's viscosimeters(20-1)-(20-4) until they reach the initial level(C) of liquid.

The samples which will be applied to the present example are glycerine. The samples filled in the respective Ostwald's viscosimeters(20-1)-(20-4) are 21% glycerine, 23% glycerine, 27% glycerine and 30% glycerine.

When testing requirements are met, a fixing bracket(25) with Ostwald's viscosimeters(20-1)-(20-4) mounted will be installed in the water bath(30) which is kept at a water temperature of 30° C.

Next, coefficients of compensation(C1) for the Ostwald's viscosimeters(20-1)-(20-4) and coefficients of compensation obtained when glycerine is produced are programmed through the computer(10) as shown in the following Table 2.

TABLE 2

|   | 1 | 2 | 3 | 4 |
|---|---|---|---|---|
| ON(Y)/OFF(F) | Y | Y | Y | Y |
| Coefficients C1 | 0.358 | 0.0267 | 0.0241 | 0.0259 |
| of compen- C2 | 2.400 | 2.400 | 2.400 | 2.400 |
| sation | | | | |
| measuring time | 45.03 | 43.30 | 49.18 | 63.82 |
| measurin number | 10 | 10 | 10 | 10 |

Here, on(Y)/off(F) is to choose one of the Ostwald's viscosimeters(20-1)-(20-4) for measurement. When one of them is chosen (Example: on(Y)), the computer(10) performs measuring operations in consecutive order through the control device(40) and obtains such measured time as shown in Table 1 and relative viscosity is calculated according to the formula(1).

The present invention improves reliability of its data by minimizing instrumental errors in measurement-(time) which vary by every measurer, makes it easy to measure a change made in a measuring sample with the passage of time due to its convenience for consecutive repeat measurement, shortens sample measuring time by being able to measure four samples successively and takes an unattended measurement of a sample after the sample is set in a viscosimeter.

We claim:

1. A viscosity measuring device using a computer, a Ostwald's viscosimeter, and a water bath, said device comprising:
    an input/output control part connected to said computer for transmitting and receiving data and control signals;
    a vacuum pump for providing vacuum pressure;
    a speed controller and motor for driving said vacuum pump;

a switching part for connecting a power source to said speed controller and motor, said switching part being connected to a first input/output port of said input/output control part;

at least one solenoid valve connected by air pressure lines to said vacuum pump and to said Ostwald's viscosimeter for controlling the presence of vacuum pressure in said Ostwald's viscosimeter;

at least one drive circuit and at least one relay for controlling said solenoid valve, said drive circuit and relay being connected to a second input/output port of said input/output control part;

a first photosensor part connected by optical fiber to a first series of signal detection ports for detecting a sample at an upper marked line of said Ostwald's viscosimeter;

a second photosensor part connected by optical fibers to a second series of signal detection ports for detecting said sample at a lower marked line of said Ostwald's viscosimeter, said first photosensor part and said second photosensor part being connected to said input/output control part;

wherein said input/output control part operates said switching part according to the position of said sample in said Ostwald's viscosimeter and when said switching part connects said power supply to said speed controller and said motor, said vacuum pump delivers vacuum pressure to said Ostwald's viscosimeter through said air pressure lines extending from said vacuum pump through said solenoid valve to a buffer tube in said Ostwald's viscosimeter, further comprising a fixing bracket for holding said Ostwald's viscosimeter, said fixing bracket having at a lower end, a fixing piece with a fixing groove and in an upper end, an adjusting piece having projecting portions disposed on opposite sides of said Ostwald's viscosimeter, whereby said optical fibers can be adjustably positioned by a connector relative to said upper marked line and said lower marked line.

2. A viscosity measuring device using a computer, a Ostwald's viscosimeter, and a water bath, said device comprising:

an input/output control part connected to said computer for transmitting and receiving data and control signals;

a vacuum pump for providing vacuum pressures a speed controller and motor for driving said vacuum pump;

a switching part for connecting a power source to said speed controller and motor, said switching part being connected to a first input/output port of said input/output control part;

at least one solenoid valve connected by air pressure lines to said vacuum pump and to said Ostwald's viscosimeter for controlling the presence of vacuum pressure in said Ostwald's viscosimeter;

at least one drive circuit and at least one relay for controlling said solenoid valve, said drive circuit and relay being connected to a second input/output port of said input/output control part;

a first photosensor part connected by optical fiber to a first series of signal detection ports for detecting a sample at an upper marked line of said Ostwald's viscosimeter;

a second photosensor part connected by optical fibers to a second series of signal detection ports for detecting said sample at a lower marked line of said Ostwald's viscosimeter, said first photosensor part and said second photosensor part being connected to said input/output control part;

wherein said input/output control part operates said switching part according to the position of said sample in said Ostwald's viscosimeter and when said switching part connects said power supply to said speed controller and said motor, said vacuum pump delivers vacuum pressure to said Ostwald's viscosimeter through said air pressure lines extending from said vacuum pump through said solenoid valve to a buffer tube in said Ostwald's viscosimeter wherein said buffer tube is cylindrical and is inserted into an open side of said Ostwald's viscosimeter and is closed by a rubber stopper for preventing said sample from back flowing into said air pressure lines.

3. A viscosity measuring device using a computer, a Ostwald's viscosimeter, and a water bath, said device comprising:

an input/output control part connected to said computer for transmitting and receiving data and control signals;

a vacuum pump for providing vacuum pressures a speed controller and motor for driving said vacuum pump;

a switching part for connecting a power source to said speed controller and motor, said switching part being connected to a first input/output port of said input/output control part;

at least one solenoid valve connected by air pressure lines to said vacuum pump and to said Ostwald's viscosimeter for controlling the presence of vacuum pressure in said Ostwald's viscosimeter;

at least one drive circuit and at least one relay for controlling said solenoid valve, said drive circuit and relay being connected to a second input/output port of said input/output control part;

a first photosensor part connected by optical fiber to a first series of signal detection ports for detecting a sample at an upper marked line of said Ostwald's viscosimeter;

a second photosensor part connected by optical fibers to a second series of signal detection ports for detecting said sample at a lower marked line of said Ostwald's viscosimeter, said first photosensor part and said second photosensor part being connected to said input/output control part;

wherein said input/output control part operates said switching part according to the position of said sample in said Ostwald's viscosimeter and when said switching part connects said power supply to said speed controller and said motor, said vacuum pump delivers vacuum pressure to said Ostwald's viscosimeter through said air pressure lines extending from said vacuum pump through said solenoid valve to a buffer tube in said Ostwald's viscosimeter, wherein when said first series of signal detection ports detects said sample at said upper marked line, pressure in said Ostwald's viscosimeter is maintained at atmosphere pressure, and when said sample flows through a capillary in said Ostwald's viscosimeter, said first series of signal detection ports detects a start signal and falling time is counted by said computer until a signal is received indicating that said sample has reached said lower marked line and a routine signal for a next operation is generated by said computer when said signal is received.

* * * * *